(12) United States Patent
Lee et al.

(10) Patent No.: US 11,187,696 B2
(45) Date of Patent: Nov. 30, 2021

(54) PHARMACEUTICAL COMPOSITION FOR TREATING OR PREVENTING OBESITY

(71) Applicant: KOREA INSTITUTE OF RADIOLOGICAL & MEDICAL SCIENCES, Seoul (KR)

(72) Inventors: Kee Ho Lee, Seoul (KR); Yang Hyun Kim, Seoul (KR); Eun Ran Park, Seoul (KR); Sung Sub Kim, Daejeon (KR); Hyun Jin Shin, Seoul (KR); Eun Ju Lee, Seoul (KR); Chun Ho Kim, Seoul (KR); Sang Jun Park, Seoul (KR); Mi-yeun Kim, Incheon (KR); Jie Young Song, Seoul (KR)

(73) Assignee: KOREA INSTITUTE OF RADIOLOGICAL & MEDICAL SCIENCES, Seoul (KR)

( * ) Notice: Subject to any disclaimer, the term of this patent is extended or adjusted under 35 U.S.C. 154(b) by 555 days.

(21) Appl. No.: 15/932,234

(22) PCT Filed: Aug. 18, 2016

(86) PCT No.: PCT/KR2016/009119
§ 371 (c)(1),
(2) Date: May 25, 2018

(87) PCT Pub. No.: WO2017/030395
PCT Pub. Date: Feb. 23, 2017

(65) Prior Publication Data
US 2018/0259502 A1   Sep. 13, 2018

(30) Foreign Application Priority Data
Aug. 18, 2015   (KR) .......................... 10-2015-0115903

(51) Int. Cl.
| | |
|---|---|
| *C12N 15/11* | (2006.01) |
| *G01N 33/50* | (2006.01) |
| *A61K 31/713* | (2006.01) |
| *C12N 15/113* | (2010.01) |
| *C12Q 1/6883* | (2018.01) |

(52) U.S. Cl.
CPC ....... *G01N 33/5008* (2013.01); *A61K 31/713* (2013.01); *C12N 15/113* (2013.01); *C12Q 1/6883* (2013.01); *G01N 33/5023* (2013.01); *C12N 2310/14* (2013.01); *C12Q 2600/136* (2013.01); *C12Q 2600/158* (2013.01)

(58) Field of Classification Search
CPC . C12N 15/113; C12N 2310/14; C12Q 1/6883
See application file for complete search history.

(56) References Cited

U.S. PATENT DOCUMENTS

| | | | | |
|---|---|---|---|---|
| 2003/0219803 | A1* | 11/2003 | Jayasena | C07H 21/00 435/6.12 |
| 2011/0008281 | A1 | 1/2011 | Liu | |
| 2011/0142820 | A1* | 6/2011 | DeMore | G01N 33/57415 424/130.1 |
| 2014/0314697 | A1* | 10/2014 | Wang | A61K 8/64 424/62 |

FOREIGN PATENT DOCUMENTS

| | | |
|---|---|---|
| KR | 20090001098 A | 1/2009 |
| KR | 10-2007-0070300 | 5/2012 |
| KR | 10-2014-0124601 | 10/2014 |
| KR | 10-2014-0125553 | 3/2015 |
| KR | 10-2015-0051524 | 10/2015 |

OTHER PUBLICATIONS

Notice of Patent Grant for Korean Patent Application KR 10-2016-0105067 dated Aug. 23, 2018.
Osorio "Looking at the epigenetic link between obesity and its consequences—the promise of EWAS" Nature Reviews Endocrinology, 2014, v 10.
De Pauw et al., "Mitochondrial (Dys)function in Adipocyte (De)differentiation and Systemic Metabolic Alterations" The American Journal of Pathology, vol. 175, No. 3, p. 927-939.
Gao et al., "CLUH regulates mitochondrial biogenesis by binding mRNAs of nuclear-encoded mitochondrial proteins" The Journal of Cell Biology, vol. 207, No. 2, p. 213-223.
Jong il Park, Master's Thesis, Department of Biotechnology, Kyunghee University, Feb. 2014.
Martel et al., "Melanophilin, a novel aldosterone-induced gene in mouse cortical collecting duct cells" Am J Physiol, Jul. 3, 2007, v 293, p. F904-F913.

\* cited by examiner

*Primary Examiner* — Ekaterina Poliakova-Georgantas
(74) *Attorney, Agent, or Firm* — Greer, Burns & Crain, Ltd.; Gregory P. Einhorn

(57) ABSTRACT

Melanophilin (MLPH) of the present invention is involved in differentiation into an adipocyte or fat accumulation, and accordingly, obesity can be treated or prevented by inhibiting the MLPH. Further, by measuring an expression level of the MLPH, obesity can be diagnosed and treated, and therapeutic agents for obesity and agents regulating differentiation into adipocytes can be screened.

12 Claims, 8 Drawing Sheets

Specification includes a Sequence Listing.

[Fig. 1]
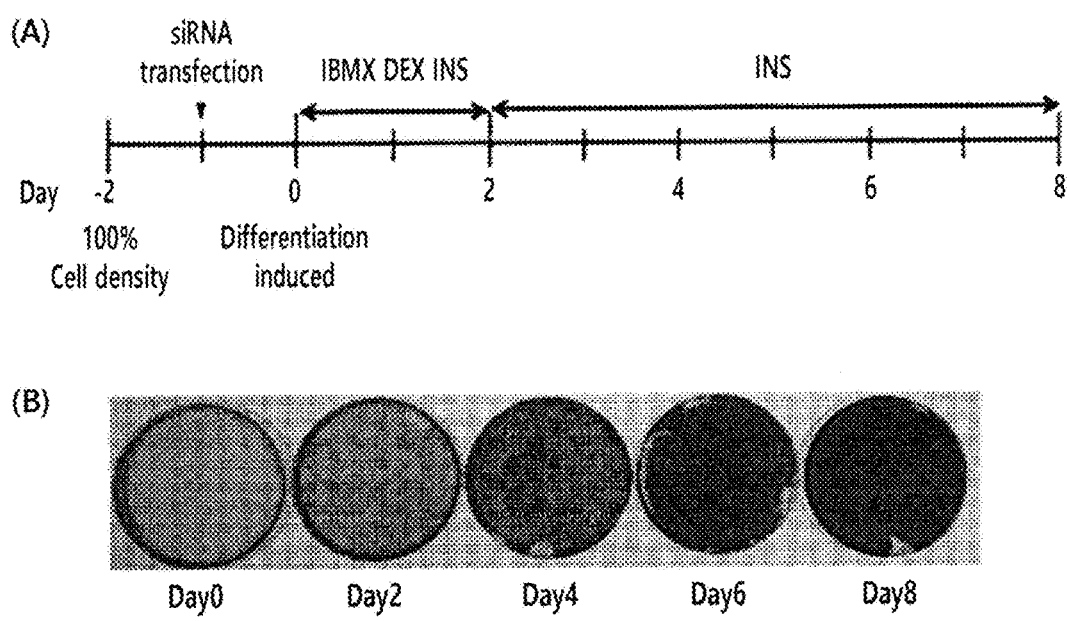

[Fig. 2]
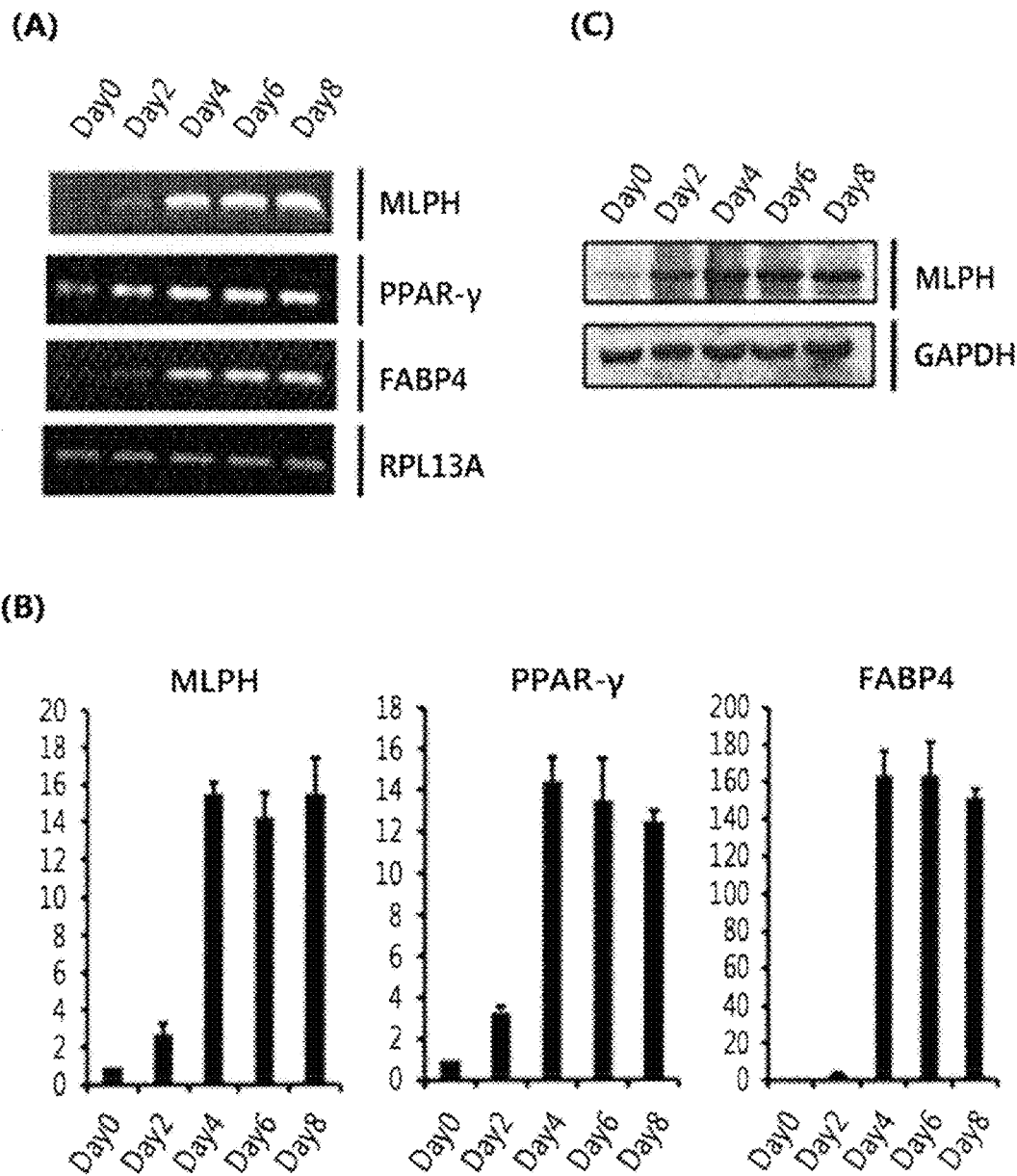

[Fig. 3]
(A)
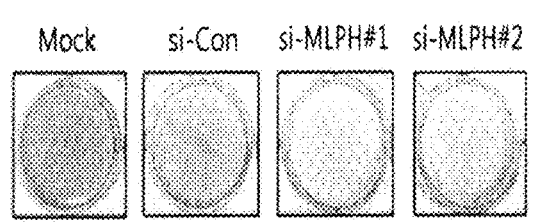
(C)
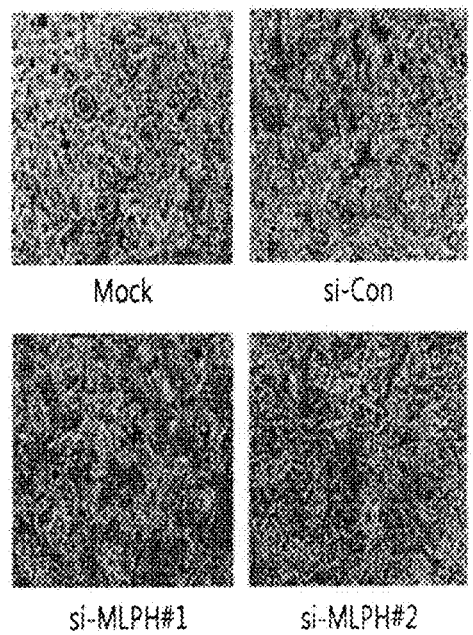
(B)
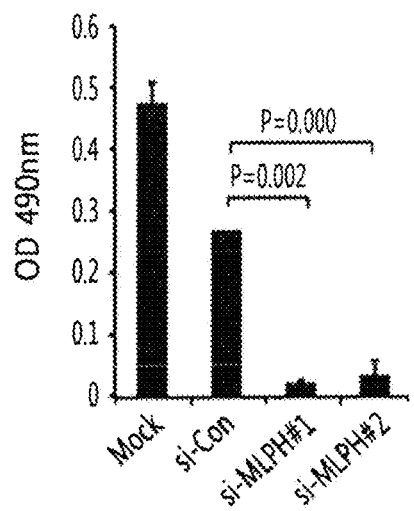

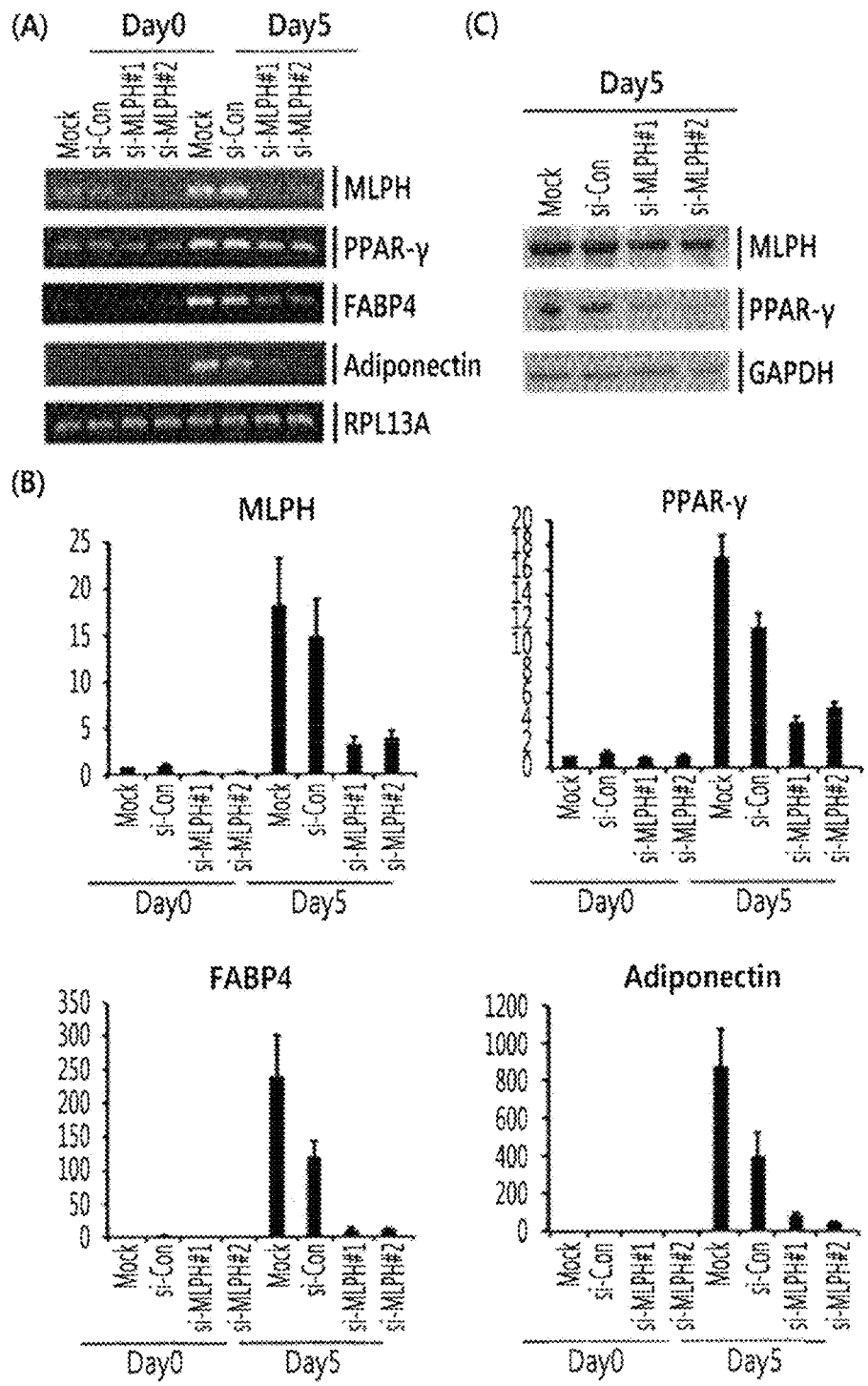

[Fig. 5]
(A)
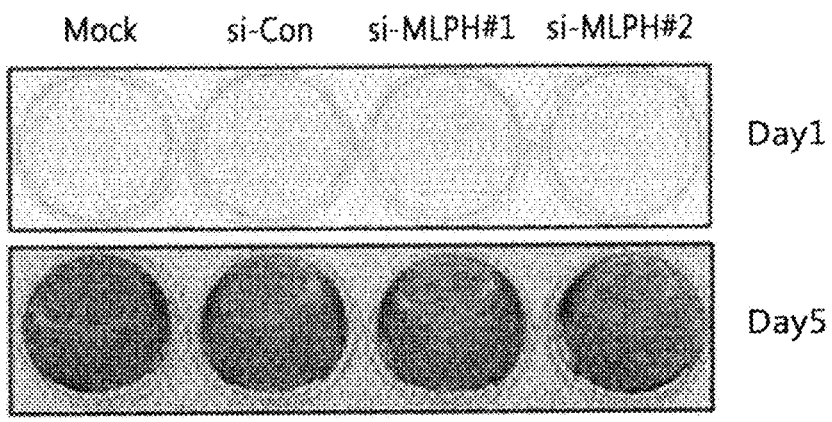
(B)
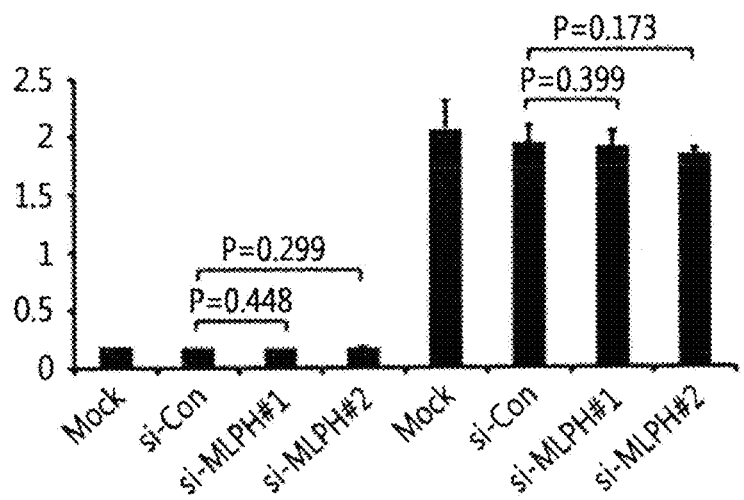
(C)
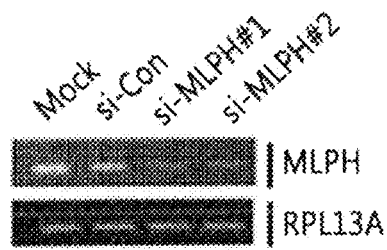

[Fig. 6]
(A)
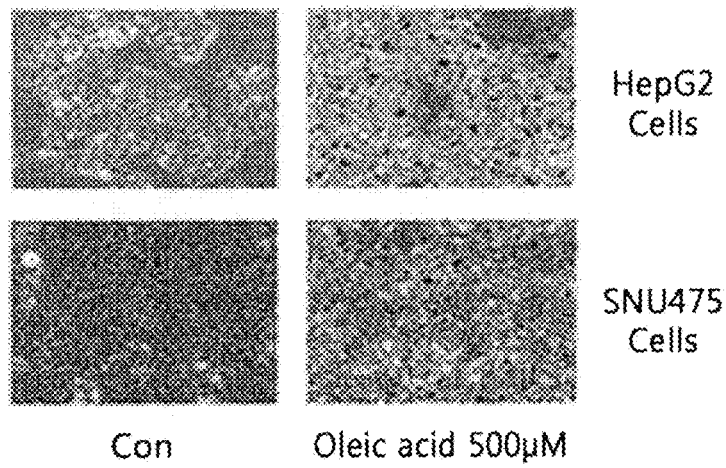
(B)
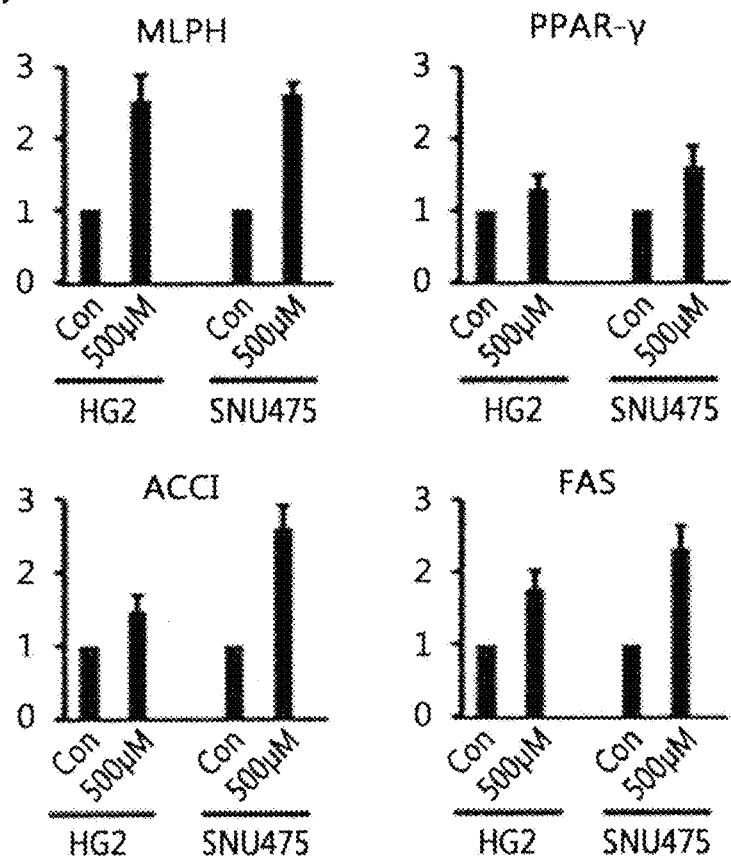

[Fig. 7]
A
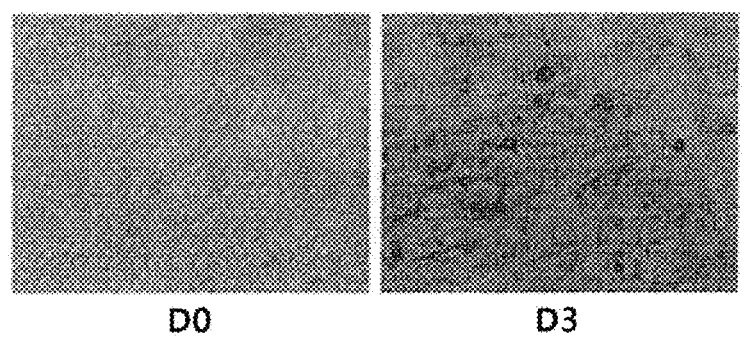
B
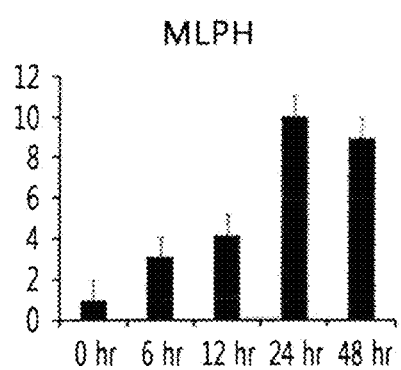
C
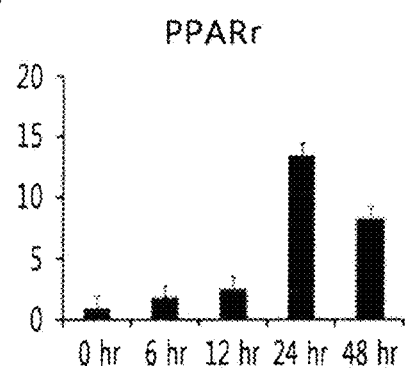

[Fig. 8]
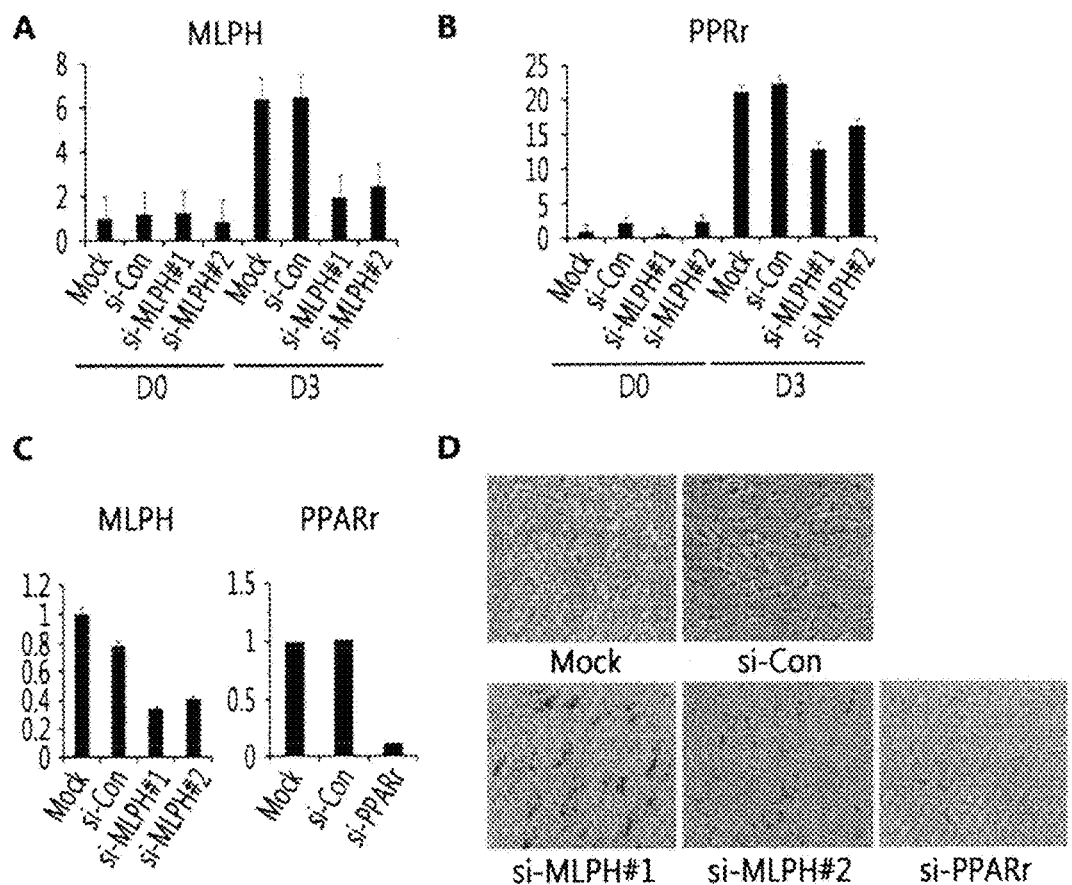

PHARMACEUTICAL COMPOSITION FOR TREATING OR PREVENTING OBESITY

RELATED APPLICATIONS

This application is a national phase application claiming benefit of priority under 35 U.S.C. § 371 to International (PCT) Patent Application serial number PCT/KR2016/009119, filed Aug. 18, 2016, which claims benefit of priority to Korean Application 10-2015-0115903, filed Aug. 18, 2015. The aforementioned applications are expressly incorporated herein by reference in their entirety and for all purposes.

REFERENCE TO SEQUENCE LISTING

A sequence listing that has been submitted on electronic form and also duplicated on paper after the abstract is part of this specification.

TECHNICAL FIELD

The present invention relates to a pharmaceutical composition for treating or preventing obesity, comprising an agent which inhibits expression or an activity of melanophilin (MLPH) protein or a gene encoding the same; a pharmaceutical composition for inhibiting or promoting differentiation into adipocytes; and a method for treating obesity comprising administering the pharmaceutical composition. Additionally, the present invention relates to a composition for diagnosing obesity, comprising an agent which measures an expression level of the protein or the gene; a method for screening a therapeutic agent for obesity or an agent regulating differentiation into adipocytes, and a method for diagnosing obesity, comprising measuring an expression level or activity of the protein or the gene. Further, the present invention relates to a kit for screening a therapeutic agent for obesity or an agent regulating differentiation into adipocytes, and a kit for examining efficacy of a therapeutic agent for obesity or an agent regulating differentiation into adipocytes, comprising an agent which measures an expression level or activity of the protein or the gene. Further, the present invention relates to a composition and a kit for detecting a marker for obesity diagnosis. Further, the present invention relates to a composition and a kit for detecting a marker for measuring a level of differentiation into adipocytes.

BACKGROUND

Obesity is a biological phenomenon caused by interaction of genetic, metabolic, environmental, and behaviorally complex factors, and is generally recognized as overweight. Medically, obesity is defined as a body mass index (BMI) of 30 (i.e., 30% or higher than average weight) or greater, or a BMI of 27 or greater. Westernized meals and a lack of exercise increase overweight and obesity in contemporary humans.

According to the World Health Organization (WHO), it has been reported that more than 1 billion people around the world are overweight, and of these, at least 3 million people are clinically obese, and more than 25,000 people die of a disease related to overweight every year. In particular, obesity is known as an important factor leading to various adult diseases such as hypertension, type II diabetes, cancer, gallbladder diseases, hyperlipidemia, arteriosclerosis, etc.

It is difficult to consider that obesity is caused only by genetic factors, and there is a spreading recognition that a complex combination of genetic and environmental factors which destroy energy balance is an important cause of obesity.

Fat stored in adipocytes is used as an important energy source in the body. As obesity progresses, however, adipocytes increase not only in number, but also in morphology including size due to synthesis of a large amount of triglycerides by excessive adipocyte differentiation. The increase in the adipocyte size is induced by synthesizing surplus energy in the form of triglycerides and storing the same. Meanwhile, it is known that the size of adipocytes can increase by about 20 times in diameter, and consequently, their volume can increase by up to thousands of times. Adipocyte size can be controlled generally by diet control, but the differentiation process of new preadipocytes into adipocytes cannot be influenced by diet control. Accordingly, it is important to control adipocyte differentiation in order to control the fundamental treatment or inhibition of obesity.

Meanwhile, although MLPH is known to be involved in the migration and stability of melanosomes (Jongil Park, Master's Thesis, Department of Biotechnology, Kyunghee University, February 2014), it is not known whether MLPH is directly involved in adipocyte differentiation.

SUMMARY

Technical Problem

The present inventors made extensive efforts to discover a pharmaceutical composition capable of preventing or treating obesity, and as a result, confirmed that obesity can be prevented or treated by inhibiting MLPH expression and a therapeutic agent for obesity can be screened by measuring the expression level thereof, thereby completing the present invention.

Technical Solution

An object of the present invention is to provide a pharmaceutical composition for treating or preventing obesity and a pharmaceutical composition which regulates differentiation into adipocytes, comprising an agent which inhibits expression or an activity of MLPH protein or a gene encoding the same.

Another object of the present invention is to provide a composition and a kit for diagnosing obesity, and a composition and a kit for measuring differentiation into adipocytes comprising an agent which measures an expression level of MLPH protein or a gene encoding the same.

Still another object of the present invention is to provide uses of MLPH protein or a gene as a marker for diagnosing obesity and for determining differentiation into adipocytes.

Still another object of the present invention is to provide a method for diagnosing obesity, and a method for determining a level of differentiation into adipocytes, comprising measuring an expression level of MLPH protein or a gene encoding the same.

Still another object of the present invention is to provide a method for screening a therapeutic agent for obesity or an agent regulating differentiation into adipocytes, comprising measuring an expression level or activity of MLPH protein or a gene encoding the same.

Still another object of the present invention is to provide a kit for screening a therapeutic agent for obesity or agent regulating differentiation into adipocytes, comprising an agent for measuring an expression level of MLPH protein or a gene encoding the same.

Still another object of the present invention is to provide a kit for examining efficacy of a therapeutic agent for obesity or an agent for measuring differentiation into adipocytes, comprising an agent for measuring an expression level of MLPH protein or a gene encoding the same.

Still another object of the present invention is to provide a composition and a kit for detecting a marker for obesity diagnosis and a marker for measuring differentiation into adipocytes, comprising an agent which measures an expression level of MLPH protein or a gene encoding the same.

Advantageous Effects

The pharmaceutical composition of the present invention can prevent or treat obesity by inhibiting differentiation into adipocytes and fat accumulation, and can further screen a therapeutic agent and an agent regulating differentiation into adipocytes by measuring an expression level of MLPH and effectively examine efficacy of an existing therapeutic agent for obesity and an agent regulating differentiation into adipocytes.

DESCRIPTION OF THE DRAWINGS

FIG. 1A-B shows a result of adipocyte differentiation induced by treating an agent inducing adipocyte differentiation.

FIG. 2A-C shows increased expression of MLPH during the differentiation into adipocyte and fat accumulation.

FIG. 3A-C shows reduced fat accumulation and adipocyte differentiation by inhibiting the MLPH expression using MLPH siRNA.

FIG. 4A-C shows reduced expression of adipocyte differentiation markers by the inhibition of MLPH expression.

FIG. 5A-C shows that si-MLPH treatment has no effect on cell division.

FIG. 6A-B shows increased MLPH expression by treatment with oleic acid.

FIG. 7A-C shows the results of Oil Red O staining and measurements of MLPH and PPARγ expressions during human mesenchymal stem cell differentiation.

FIG. 8A-D shows the results of the MLPH and PPARγ expression measurements and Oil Red O staining under the MLPH expression-inhibited condition.

DETAILED DESCRIPTION

Best Mode

In order to achieve the above-described objects, an aspect of the present invention provides a pharmaceutical composition for treating or preventing obesity, comprising an agent which inhibits expression or an activity of MLPH protein or a gene encoding the same.

As used herein, the term "melanophilin (MLPH)" means a carrier protein known to be involved in the transport of melanosome pigments. The information of a specific nucleotide sequence of the MLPH gene or an amino acid sequence encoded by the gene can be obtained from known database such as NCBI GenBank (e.g., NM_053015.3. and NP_443748.2.). However, in addition to the known sequence, a homologous or mutated protein thereof can also be included in the MLPH range provided in the present invention, as long as the protein, identically to the MLPH, can show the effect of inducing adipocyte differentiation and fat accumulation.

As used herein, the term "homology" refers to the degree of similarity of a sequence to an amino acid sequence of a wild-type protein or nucleotide sequence encoding the same, and includes a sequence having said or higher sequence homology to the amino acid sequence or nucleotide sequence of the present invention. The homology may be determined by comparing with the naked eye, but also using a bioinformatic algorithm which provides analysis results of a degree of homology of target sequences by aligning them in parallel for comparison. The homology between the two amino acid sequences may be indicated as percentages. Useful automated algorithms may be used in GAP, BEST-FIT, FASTA, and TFASTA computer software modules of the Wisconsin Genetics Software Package (Genetics Computer Group, Madison, Wis., USA). The alignment algorithms automated in these modules include the Needleman & Wunsch, the Pearson & Lipman, and the Smith & Waterman sequence alignment algorithms. Other useful algorithms and homology determinations on alignment are already automated in software such as FASTP, BLAST, BLAST2, PSIBLAST, and CLUSTAL W.

As used herein, the term "agent capable of inhibiting expression or an activity" refers to a substance capable of inhibiting a transcript or protein expressed and produced from a gene. The agent may be a transcript factor which binds to the gene and inhibits in a transcription level; a short interfering RNA (e.g., miRNA, siRNA, and shRNA) which binds to a transcript that has been transcribed and synthesized and degrades the transcript; and a compound which inhibits the MLPH expression or activity, for example, a low-molecular weight compound; an antibody, aptamer, and antagonist capable of binding to an expressed protein, etc., but is not limited thereto.

As used herein, the term "short interfering RNA" refers to double-stranded RNA capable of inducing RNAi which inhibits activity of an RNA gene. In the present invention, the short interfering RNA may be miRNA, siRNA, shRNA, etc. capable of inhibiting the MLPH expression, and may be in any form as long as it inhibits the MLPH gene expression or activity. For instance, siRNA obtained by chemical, biochemical, or in vivo synthesis, double-stranded RNA of 10 nucleotides decomposed from double-stranded RNA of at least 40 nucleotides, etc. may be used. Specifically, siRNA inhibiting the MLPH expression is siRNA of SEQ ID NO: 39 or 40, etc., but is not limited thereto.

The interfering RNA may consist of a sequence specifically having a homology to part of a gene encoding each protein of, but not limited to, about 70% or above, 75% or above, 80% or above, 85% or above, 90% or above, 95% or above, or 100%, and may use RNA including a double-stranded region or a variant thereof.

As used herein, the term "low-molecular weight compound" may be included without limitation in the present invention as long as it can inhibit the MLPH expression or activity, and may be a substance which is naturally derived or synthesized. Specifically, it may be an organic synthetic substance or a natural substance.

As used herein, the term "antibody" refers to a proteinaceous molecule capable of specifically binding to an antigenic region of a protein or peptide molecule. The antibody may be manufactured by a conventional method from a protein, which is obtained from an expression vector into which a marker gene encoding the protein is cloned according to the conventional method. Although not particularly limited thereto, the form of the antibody may be a polyclonal antibody, a monoclonal antibody, or a part thereof as long as it has antigenicity, and any immunoglobulin antibody as well as a specific antibody such as a humanized antibody. Additionally, the antibody includes not only a complete form of an antibody having two full-length light chains and two full-length heavy chains but also a functional fragment of the antibody molecule. The functional fragment of the antibody refers to a fragment possessing at least an antigen-binding function, and may be Fab, F(ab'), F(ab') 2, and Fv. With regard to the purpose of the present invention, the antibody may be an antibody capable of specifically binding to the MLPH protein.

As used herein, the term "aptamer" refers to a nucleic acid molecule having a binding activity to a target molecule. The aptamer can be RNA, DNA, a modified nucleic acid, or a mixture thereof, and can be in a linear or cyclic form. Mostly, it is known that the shorter the nucleotide sequence consisting of the aptamer, the easier its chemical synthesis and mass production, and that such aptamers have excellent in vivo stability and low toxicity.

With regard to the purpose of the present invention, the aptamer can be understood as a means of inhibiting the protein activity by binding to the MLPH protein.

As used herein, the term "antagonist" refers to a molecule capable of directly or indirectly reducing biological activity of a receptor, and includes molecules that can reduce the ligand action when used with the ligand of the receptor, but is not limited thereto.

With regard to the purpose of the present invention, the antagonist includes molecules without limitation as long as the molecules inhibit the MLPH protein activity, and as a specific example, the antagonist can be a molecule inhibiting MLPH activity, but is not limited thereto.

As used herein, the term "obesity" refers to a condition or disease in which excessive fat is accumulated due to energy imbalance. By administering the pharmaceutical composition of the present invention to a subject, weight is lost and obesity can be prevented or treated.

As used herein, the term "prevention" refers to all behaviors involved in inhibition or delay of the development of obesity by administration of the pharmaceutical composition of the present invention.

According to an exemplary embodiment of the present invention, as a result of determining the relationship between the differentiation into adipocytes and MLPH using the 3T3-L1 cell lines, it was confirmed that the expressions of PPARγ, FABP4, etc. (regulatory factors for adipogenic differentiation) as well as MLPH increased during the differentiation into adipocytes (FIG. 2).

According to another exemplary embodiment of the present invention, as a result of inhibiting the MLPH using siRNA, it was confirmed that the differentiation into adipocytes was inhibited and fat accumulation was reduced (FIG. 3). Further, it was confirmed that the treatment with the siRNA would not affect the cell proliferation and that the differentiation into adipocytes is an effect due to the MLPH inhibition, not due to the cytotoxicity of siRNA (FIG. 5).

According to another exemplary embodiment of the present invention, as a result of measuring the MLPH expression after treatment of the liver cancer cell line with oleic acid, the MLPH expression was increased and fat was efficiently accumulated due to the oleic acid treatment (FIG. 6).

In this regard, it could be understood that as the MLPH is involved in the differentiation into adipocytes and fat accumulation and thus controls the MLPH expression, it can prevent or treat obesity; further, obesity can be diagnosed and a therapeutic agent for obesity can be screened by measuring the MLPH expression level.

According to another exemplary embodiment of the present invention, as a result of measuring Oil Red staining and an MLPH expression level during the differentiation of human mesenchymal stem cell into adipocytes, red staining was observed due to the Oil Red staining, and the MLPH expression was increased (FIG. 7).

According to another exemplary embodiment of the present invention, as a result of inducing the adipocyte differentiation of the human cells under the condition in which the MLPH expression was inhibited, the expression of the adipocyte differentiation marker PPARγ was reduced and the degree of the Oil Red O staining was significantly decreased by the inhibition of the MLPH expression (FIG. 8).

Accordingly, it was confirmed that the MLPH is involved in differentiation into adipocytes and fat accumulation in the human cells, and can be used in the prevention or treatment of obesity by controlling the MLPH expression.

The pharmaceutical composition of the present invention can be formulated in the form of a pharmaceutical composition for treating or preventing obesity which further includes an appropriate carrier, excipient, or diluent that is conventionally used in the preparation of a pharmaceutical composition. The carrier may include a non-naturally occurring carrier. Specifically, the pharmaceutical composition may be prepared into an oral formulation such as a powder, granule, tablet, capsule, suspension, emulsion, syrup, or aerosol, an external formulation, a suppository formulation, and a sterilized injection solution formation, according to conventional methods. The carriers, excipient, and diluents that can be contained in the pharmaceutical composition may be lactose, dextrose, sucrose, sorbitol, mannitol, xylitol, erythritol, maltitol, starch, Acacia rubber, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate, and mineral oils. The pharmaceutical composition is prepared into a formulation using a commonly used diluent or excipient such as a filler, extender, binding agent, wetting agent, disintegrant, surfactant, etc. Solid formulations for oral administration may include a tablet, pill, powder, granule, capsule, etc., and are prepared by mixing at least one excipient, e.g., starch, calcium carbonate, sucrose, lactose, gelatin, etc. In addition to the simple excipient, a lubricant such as magnesium stearate and talc may also be used. Liquid formulations for oral administration may include a suspension, a liquid medicine for internal use, an emulsion, a syrup, etc. In addition to a commonly used simple diluent such as water and liquid paraffin, various excipients such as a wetting agent, sweetener, aromatic, preservative, etc. may also be contained. Formulations for parenteral administration may include a sterilized aqueous solution, non-aqueous solution, suspension, emulsion, lyophilized formulation, and suppository. The non-aqueous solution or suspension may contain propylene glycol, polyethylene glycol, a vegetable oil such as olive oil, an injectable ester such as ethyl oleate, etc. Witepsol, macrogol, tween 61, cocoa butter, laurin butter, glycerogelatin, etc. may be used as a base of the suppository.

The amount of the agent contained in the pharmaceutical composition of the present invention may be in the range from 0.0001 wt % to 50 wt % relative to the total weight of the total composition, and more preferably, 0.01 wt % to 10 wt %, but is not particularly limited thereto.

The pharmaceutical composition of the present invention may be administered in a pharmaceutically effective amount. As used herein, the term "pharmaceutically effective amount" refers to an amount sufficient for the treatment of diseases at a reasonable benefit/risk ratio applicable to a medical treatment, and the level of the effective dose may be determined from factors including severity of illness, drug activity, age, body weight, health conditions, drug sensitivity of a subject, administration time, administration route and dissolution rate, length of treatment of the pharmaceutical composition of the present invention, drug(s) used in combination with or simultaneously with the pharmaceutical composition of the present invention, and other factors well known in the medical field. The pharmaceutical composition of the present invention may be administered as an individual therapeutic agent or in combination with other therapeutic agent(s), and also sequentially or simultaneously with the conventional therapeutic agent(s). Additionally, the pharmaceutical composition of the present invention may be administered as a single dose or in multiple divided doses. It is important that the least amount which can achieve the maximum effect without any side effects be administered in consideration of all of the factors described above.

The administration dose of the pharmaceutical composition of the present invention may be determined by those skilled in the art considering purpose of use, severity of the disease, the age, body weight, sex, and anamnesis of the subject, or the type of a substance used as an active ingredient. For example, the pharmaceutical composition of the present invention may be administered to mammals, including humans, in a daily dose of 10 mg/kg to 100 mg/kg, preferably 10 mg/kg to 30 mg/kg. The administration frequency of the present invention may be, but is not particularly limited to, one to three times per day, or divided into several doses.

As still another aspect, the present invention provides a method for preventing or treating obesity, comprising administering the composition for treating or preventing obesity to a subject at risk of obesity.

As used herein, the term "prevention" is as previously described.

As used herein, the term "treatment" refers to all behaviors which would ameliorate symptoms of obesity or change the same to beneficial states by administering the pharmaceutical composition of the present invention.

As a method for preventing or treating obesity comprising administering the pharmaceutical composition for treating or preventing obesity of the present invention, the symptoms of obesity can be ameliorated or become beneficial in a subject with obesity, or the onset of obesity can be inhibited in a subject at risk of developing obesity.

As still another aspect, the present invention provides a composition for diagnosing obesity, comprising an agent which measures an expression level of MLPH protein or a gene encoding the same.

As used herein, "melanophilin (MLPH)" is as previously described.

As used herein, the term "agent which measures an expression level of MLPH protein or a gene encoding the same" may specifically be one selected from the group consisting of an anti-sense oligonucleotide, a pair of primers, and a probe, which specifically binds to mRNA of the MLPH gene, and a combination thereof; or that consisting of an antibody, an aptamer, and an antagonist, which specifically bind to the MLPH protein, and a combination thereof, but is not limited thereto.

The antibody, aptamer, and antagonist are the same as previously described.

As used herein, the term "primer" refers to a nucleic acid sequence having a short free 3' hydroxyl group; can form base pairs with a complementary template; and indicates a short nucleic acid sequence functioning as a starting point for the template strand transcription. The primer can initiate DNA synthesis under the presence of four different nucleoside triphosphates and a reagent for polymerization (that is, DNA polymerase or reverse transcriptase) in a proper buffer solution and at a proper temperature. PCR conditions and lengths of sense and anti-sense primers can be modified on the basis of the methods known in the art. Additionally, the primers can be modified, and such modification may include methylation, capping, substitution of a nucleotide, and modification between nucleotides, for example, modification into an uncharged linker (e.g., methyl phosphonate, phosphotriester, phosphoroamidate, and carbamate) or charged linker (e.g., phosphorothioate, phosphorodithioate). Further, in order to more effectively recognize PCR products amplified using the pair of primers, the 5' or 3' end of the primers may be marked with a fluorescent marker material, etc. The fluorescent marker material is not limited thereto, but may be FAM (6-carboxyfluorescein), HEX (2',4',5',7',-tetrachloro-(6-carboxy-4,7-dichlorofluorescein), NED™, etc. Specifically, the primers of the present invention may be selected from the group consisting of SEQ ID NOS: 1 to 38, but are not limited thereto.

As used herein, the term "probe" refers to a nucleic acid fragment such as RNA or DNA capable of specifically binding to a gene or mRNA, ranging from several to hundreds of bases in length. The probe may be prepared in the form of an oligonucleotide probe, single-stranded DNA probe, double-stranded DNA probe, RNA probe, etc., and can be labeled so as to be detected.

As used herein, "diagnosis" refers to identifying the presence or characteristics of a pathological condition. With regard to the purpose of the present invention, the diagnosis may refer to identifying the onset of obesity.

Using the composition for diagnosing obesity of the present invention, obesity can be diagnosed when a subject suspected of having obesity, compared to a healthy individual, shows an increased expression level of the MLPH protein or gene encoding the same upon measuring the expression level of each of the MLPH protein of a sample isolated from the subject suspected of having obesity and a healthy person and the gene encoding the same. The healthy individual refers to one who is not obese.

As still another aspect, the present invention provides a kit for diagnosing obesity comprising the composition for diagnosing obesity.

The "kit" of the present invention may further include an instruction guide where the optimal conditions for performing the reaction are described. The instruction guide includes explanations in a guide book such as a pamphlet or a leaflet, a label attached to a kit, and on the surface of a package containing the kit. Additionally, the instruction guide may include information being published or provided through an electric medium such as an internet.

The kit may be a RT-PCR kit, a kit for DNA diagnosis (e.g., DNA chip), or a protein chip kit.

As a specific embodiment, the kit of the present invention may be a kit including an essential element necessary to perform the RT-PCR. The RT-PCR kit may include test tubes or other appropriate containers, reaction buffers (pH and magnesium concentration may vary), deoxynucleotides (dNTPs), enzymes such as Taq-polymerase and reverse transcriptase, DNase inhibitor, RNase inhibitor, DEPC-water, sterile water, etc. in addition to each pair of primers specific to MLPH. Additionally, a pair of primers specific to a gene used as a quantification control may be included.

The DNA chip kit is generally a flat solid support plate, and includes nucleic acid species attached to a surface of glass smaller than a slide glass for a microscope in a gridded array. In the kit, the nucleic acids are uniformly arranged on the chip surface, and multi-hybridization takes place between the nucleic acids on the DNA chip and complementary nucleic acids contained in a solution treated on the chip surface, thereby facilitating a large volume of parallel analysis.

The protein kit may be a kit in which one or more antibodies against the marker are arranged and fixed at a high density at predetermined positions on a substrate. A method for using a protein chip includes isolating protein from a sample and hybridizing the isolated protein with the protein chip to form an antigen-antibody complex, which is then read to examine the presence or expression level of the protein.

Obesity can be determined by measuring the expression level of the MLPH protein or gene encoding the same in a subject suspected of obesity using the kit for diagnosing obesity of the present invention.

As still another aspect, the present invention provides a composition for inhibiting adipocyte differentiation, comprising an agent which inhibits expression or an activity of MLPH protein or a gene encoding the same.

As used herein, the term "agent which inhibits expression or an activity of MLPH protein or a gene encoding the same" is as previously described.

The composition for inhibiting adipocyte differentiation of the present invention can inhibit the differentiation into adipocytes by inhibiting the expression or activity of MLPH.

As still another aspect, the present invention provides a method for diagnosing obesity, comprising measuring an expression level of MLPH protein or a gene encoding the same.

The "method for diagnosing obesity" of the present invention diagnoses obesity when a subject suspected of having obesity, compared to a healthy individual, shows an increased expression level of the MLPH protein or gene encoding the same upon measuring the expression level of each of the MLPH protein or gene encoding the same of a sample isolated from the subject suspected of having obesity and healthy person and the gene encoding the same. The healthy individual refers to one who is not obese.

The expression level of the MLPH protein or gene encoding the same may be measured using an anti-sense oligonucleotide, a pair of primers, and a probe, which specifically bind to mRNA of the MLPH gene; or an antibody, an aptamer, and an antagonist, which specifically bind to the MLPH protein, but is not limited thereto.

As used herein, the term "subject" refers to all animals including humans, having a risk of developing obesity or having obesity.

As used herein, the term "isolated sample" refers to a sample which is isolated from the subject and includes the MLPH protein or mRNA of the gene encoding the same, thereby enabling measurement of the expression level of the protein and gene. The sample is not particularly limited thereto, but may be an isolated tissue or isolated cell.

As still another aspect, the present invention provides a method for screening a therapeutic agent for obesity, comprising (a) treating a candidate therapeutic agent for obesity in a cell in which MLPH gene is expressed; (b) measuring an expression level or activity of MLPH protein or a gene encoding the same in the cell treated with the candidate therapeutic agent for obesity in (a); and (c) determining the candidate therapeutic agent for obesity as a therapeutic agent for obesity in a case where the expression level or activity measured in (b) decreases compared to that of a control not treated with the candidate therapeutic agent.

As used herein, the term "therapeutic agent for obesity" refers to a substance which induces inhibition of differentiation into adipocytes in an obese subject and thus has effects of reducing body fat, inhibiting fat accumulation, losing weight, etc. It can be a nucleic acid, protein, extract or natural product, or compound; specifically, a low-molecular weight compound, organic synthetic substance, natural substance, microRNA, siRNA, shRNA, an antibody, aptamer, etc., but is not limited thereto.

As used herein, the term "candidate therapeutic agent for obesity" refers to a substance capable of becoming a therapeutic agent for obesity as above, and is presumed to have an ability to treat obesity according to a conventional selection method, or may be a randomly selected individual nucleic acid, protein, peptide, extract or natural product, or compound, specifically, a low-molecular weight compound, organic synthetic substance, natural substance, microRNA, siRNA, shRNA, antibody, aptamer, etc., but is not limited thereto.

Measuring an expression level of a protein or gene encoding the same in the present invention may refer to measuring an expression level of the MLPH protein or mRNA level of the MLPH gene.

Specifically, measuring the mRNA expression level of the MLPH gene may use an anti-sense oligonucleotide, a pair of primers, or a probe, which specifically binds to mRNA of the MLPH gene, or a combination thereof, using an analytical method selected from the group consisting of RT-PCR, competitive RT-PCR, real-time RT-PCR, RNase protection assay, Northern blotting, and DNA microarray chip assay, but is not limited thereto.

Additionally, measuring the expression level of the MLPH protein may use an antibody, aptamer, or antagonist, which specifically binds to the protein, or a combination thereof, using an analytical method selected from the group consisting of Western blotting, ELISA, radioimmunoassay, radial immunodiffusion, Ouchterlony immunodiffusion, rocket immunoelectrophoresis, immunohistostaining, immunoprecipitation assay, complement fixation assay, FACS, and protein chip, but is not limited thereto.

As used herein, the term "control group" refers to MLPH-expressing cells or tissues which are not treated with the candidate therapeutic agent for obesity and to cells or tissues in a parallel relation with the group treated with the candidate.

As used herein, the term "method for screening a therapeutic agent for obesity" was designed to compare the activity and expression of MLPH with the control group cells treated with no candidate adipocyte differentiation inhibitor based on observations in which the MLPH expression is involved in the differentiation into adipocytes. The expression level of the gene or protein encoded by the gene of the present invention is measured in the absence of the candidate therapeutic agent for preventing or treating obesity and in the presence of the same, and then, the expression levels are compared. If the expression level of the gene or protein encoding the same measured in the presence of the candidate is reduced compared to that in the absence of the candidate, the candidate can be predicted to be a therapeutic agent for preventing or treating obesity.

A substance obtained by such screening method is applied to the further development of a prophylactic or therapeutic agent as a leading compound. By modifying and optimizing the structure of the leading compound to allow it to exhibit the inhibitory effect against MLPH or a gene encoding the same, a novel prophylactic or therapeutic agent can be developed. Such leading compound would show a partial or complete activity-inhibitory effect against the MLPH or gene encoding the same, and thus can prevent or treat obesity-related diseases.

As still another aspect, the present invention provides a kit for screening a therapeutic agent for obesity, comprising an agent which measures an expression level of MLPH protein or a gene encoding the same.

Using the kit of the present invention for screening a therapeutic agent for obesity, an agent for obesity can be selected from candidate therapeutic agents for obesity.

In the present invention, the agent which measures an expression level of MLPH protein or a gene encoding the same, and the kit are the same as previously described.

As still another aspect, the present invention provides a kit for examining efficacy of a therapeutic agent for obesity, comprising an agent which measures an expression level of MLPH protein or a gene encoding the same.

In the present invention, the agent which measures an expression level of MLPH protein or a gene encoding the same and the kit are the same as previously described.

The "kit for examining efficacy of a therapeutic agent for obesity" of the present invention includes an agent which measures an expression level of MLPH protein or a gene encoding the same, and may be a kit capable of measuring an expression level of MLPH protein or a gene encoding the same in an MLPH-expressing cell treated with the therapeutic agent for obesity. The lower the MLPH expression level measured, it can be determined to be a more effective therapeutic agent for obesity.

The "kit for examining efficacy of a therapeutic agent for obesity" of the present invention includes an agent which measures an expression level of MLPH protein or a gene encoding the same, and may be a kit capable of measuring an expression level of MLPH protein or a gene encoding the same in an MLPH-expressing cell treated with the therapeutic agent for obesity. The lower the MLPH expression level measured, it can be determined to be a more effective therapeutic agent for obesity.

As still another aspect, the present invention provides a method for screening an adipocyte differentiation promoting agent, comprising (a) treating a candidate adipocyte differentiation promoting agent in a cell in which MLPH gene is expressed; (b) measuring an expression level or activity of MLPH protein or a gene encoding the same in the cell treated with the candidate adipocyte differentiation promoting agent in (a); and (c) determining the candidate adipocyte differentiation promoting agent as an adipocyte differentiation promoting agent in a case where the expression level or activity measured in (b) increases compared to that of a control not treated with the candidate adipocyte differentiation promoting agent.

As used herein, the term "agent regulating adipocyte differentiation" refers to all substances (nucleic acids, proteins, other extracts or natural products, compounds, etc.) capable of promoting or inhibiting the differentiation into adipocytes. Specifically, any substance can be included as the agent regulating differentiation into adipocytes in the present invention as long as it can induce overexpression of MLPH or inhibit the expression of MLPH, thereby promoting or inhibiting the differentiation into adipocytes, or can significantly influence the expression level of MLPH during the promotion or inhibition of the differentiation into adipocytes. The "adipocyte differentiation promoting agent" and "adipocyte differentiation inhibitor" are included in the "agent regulating adipocyte differentiation".

As used herein, the term "candidate adipocyte differentiation promoting agent" is presumed to have an ability to promote adipocyte differentiation according to a conventional selection method, or may be a randomly selected individual nucleic acid, protein, extract or natural product, or compound, specifically, a low-molecular weight compound, organic synthetic substance, natural substance, microRNA, siRNA, shRNA, antibody, aptamer, etc., but is not limited thereto.

As used herein, the terms "measurement of an expression level of protein or a gene encoding the same" and "control group" are as previously described.

As used herein, the term "method for screening an adipocyte differentiation promoting agent" was designed to compare the activity and expression of MLPH with the control group cells treated with no candidate adipocyte differentiation promoting agent based on observations in which MLPH expression is involved in the differentiation into adipocytes. The expression level of the gene or protein encoded by the gene of the present invention is measured in the absence of the candidate adipocyte differentiation promoting agent and in the presence of the same, and then, the expression levels are compared. If the expression level of the gene or protein encoding the same measured in the presence of the candidate is increased compared to that in the absence of the candidate, the candidate can be predicted to be an adipocyte differentiation promoting agent.

As still another aspect, the present invention provides a method for screening an adipocyte differentiation inhibitor, comprising (a) treating a candidate adipocyte differentiation inhibitor in a cell in which MLPH gene is expressed; (b) measuring an expression level or activity of MLPH protein or a gene encoding the same in the cell treated with the candidate adipocyte differentiation inhibitor in (a); and (c) determining the candidate adipocyte differentiation inhibitor as an adipocyte differentiation inhibitor in a case where the expression level or activity measured in (b) decreases compared to that of a control not treated with the candidate adipocyte differentiation inhibitor.

As used herein, the term "candidate adipocyte differentiation inhibitor" is presumed to have an ability to inhibit adipocyte differentiation according to a conventional selection method, or may be a randomly selected individual nucleic acid, protein, extract or natural product, or compound, specifically, a low-molecular weight compound, organic synthetic substance, natural substance, microRNA, siRNA, shRNA, antibody, aptamer, etc., but is not limited thereto.

As used herein, the terms "measurement of an expression level of protein or a gene encoding the same" and "control group" are as previously described.

As used herein, the term "method for screening an adipocyte differentiation inhibitor" was designed to compare the activity and expression of MLPH with the control group cells treated with no candidate adipocyte differentiation inhibitor based on observations in which the MLPH expression is involved in the differentiation into adipocytes. The expression level of the gene or protein encoding the same of the present invention is measured in the absence of the candidate adipocyte differentiation inhibitor and in the presence of the same, and then, the expression levels are compared. If the expression level of the gene or protein encoding the same measured in the presence of the candidate is reduced compared to that in the absence of the candidate, the candidate can be predicted to be an adipocyte differentiation inhibitor.

A substance obtained by such screening method can be used as an adipocyte differentiation inhibitor, in particular in the prevention or treatment of obesity.

As still another aspect, the present invention provides a kit for screening an adipocyte differentiation promoting agent, comprising an agent which measures an expression level of MLPH protein or a gene encoding the same.

Using the kit of the present invention for screening an adipocyte differentiation promoting agent, an adipocyte differentiation promoting agent can be selected from candidate adipocyte differentiation promoting agents.

In the present invention, the agent which measures an expression level of MLPH protein or a gene encoding the same and the kit are the same as previously described.

As still another aspect, the present invention provides a kit for screening an adipocyte differentiation inhibitor, comprising an agent which measures an expression level of MLPH protein or a gene encoding the same.

Using the kit of the present invention for screening an adipocyte differentiation inhibitor, an adipocyte differentiation inhibitor can be selected from candidate adipocyte differentiation inhibitors.

As used herein, the terms "agent which measures an expression level of MLPH protein or a gene encoding the same" and "kit" are as previously described.

As still another aspect, the present invention provides a kit for examining efficacy of an adipocyte differentiation promoting agent, comprising an agent which measures an expression level of MLPH protein or a gene encoding the same.

As used herein, the terms "agent which measures an expression level of MLPH protein or a gene encoding the same", "adipocyte differentiation promoting agent", and "kit" are as previously described.

The "kit for examining efficacy of an adipocyte differentiation promoting agent" of the present invention includes an agent which measures an expression level of MLPH protein or a gene encoding the same, and may be a kit capable of measuring an expression level of MLPH protein or a gene encoding the same in an MLPH-expressing cell treated with the adipocyte differentiation promoting agent. The higher the MLPH expression level measured, it can be determined to be a more effective adipocyte differentiation promoting agent. Such kit for examining efficacy can be useful in the examination of titer of the adipocyte differentiation promoting agent during general adipocyte differentiation, etc.

As still another aspect, the present invention provides a kit for examining efficacy of an adipocyte differentiation inhibitor, comprising an agent which measures an expression level of MLPH protein or a gene encoding the same.

As used herein, the terms "agent which measures an expression level of MLPH protein or a gene encoding the same", "adipocyte differentiation inhibitor", and "kit" are as previously described.

The "kit for examining efficacy of an adipocyte differentiation inhibitor" of the present invention includes an agent which measures an expression level of MLPH protein or a gene encoding the same, and may be a kit capable of measuring an expression level of MLPH protein or a gene encoding the same in an MLPH-expressing cell treated with the adipocyte differentiation inhibitor. The lower the MLPH expression level measured, it can be determined to be a more effective adipocyte differentiation inhibitor. Such kit for examining efficacy can be useful in the examination of titer of the adipocyte differentiation inhibitor during general adipocyte differentiation, etc.

As still another aspect, the present invention provides a composition for detecting a marker for obesity diagnosis, comprising an agent which measures expression or an activity of MLPH protein or a gene encoding the same.

In the present invention, the "agent which measures expression or an activity of MLPH protein or a gene encoding the same" is as previously described.

As used herein, the term "maker for obesity diagnosis" may refer to an organic biomolecule which shows significant difference in the expression level between a healthy individual and an obese subject.

Using the composition for detecting a marker for obesity diagnosis, a marker for obesity diagnosis which shows significant difference in the expression level between an obese subject and a subject who is not obese can be detected.

As still another aspect, the present invention provides a kit for detecting a marker for obesity diagnosis, comprising the composition for detecting the marker for obesity diagnosis.

As used herein, the terms "agent which measures an expression level of MLPH protein or a gene encoding the same", "marker for obesity diagnosis", "composition for detecting a marker for obesity diagnosis", and "kit" are as previously described.

Using the kit of the present invention for detecting a marker for obesity diagnosis, a marker which shows significant difference in expression level compared to the control group sample can be detected.

As still another aspect, the present invention provides use of the pharmaceutical composition in the preparation of a drug for preventing or treating obesity.

As still another aspect, the present invention provides use of the marker for obesity diagnosis of the MLPH protein or gene.

As still another aspect, the present invention provides a composition for promoting adipocyte differentiation, comprising an agent which overexpresses the MLPH protein or gene encoding the same.

As used herein, the term "agent which overexpresses the MLPH protein or gene encoding the same" refers without limitation to any material as long as it can increase the MLPH expression to promote the differentiation into adipocytes, and may be a nucleic acid, protein, extract or natural product, compound, etc., specifically, a low-molecular weight compound, organic synthetic substance, natural substance, etc., but is not limited thereto.

The composition for promoting adipocyte differentiation of the present invention can promote the differentiation into adipocytes through the MLPH overexpression.

As still another aspect, the present invention provides a composition for detecting a marker for diagnosing differentiation into adipocytes, comprising an agent which measures an expression level of MLPH protein or a gene encoding the same.

As used herein, the terms "agent which measures measuring an expression level of MLPH protein or a gene encoding the same" and "marker" are as previously described.

As used herein, the term "marker for diagnosing differentiation into adipocytes" refers to an organic biomolecule which shows significant difference in the expression level as adipocyte differentiation progresses.

The composition for detecting a marker for diagnosing differentiation into adipocytes can detect an organic biomolecule which shows difference in the marker expression at a level equivalent to or greater than that in the MLPH expression.

As still another aspect, the present invention provides a kit for determining differentiation into an adipocyte, comprising an agent which measures an expression level of MLPH protein or a gene encoding the same.

As used herein, the term "agent which measures which measures an expression level of MLPH protein or a gene encoding the same" and "kit" are the same as previously described.

The kit for determining differentiation into adipocytes according to the present invention measures the expression level of MLPH to measure and determine a progress of differentiation into adipocytes.

EXAMPLES

Mode for Invention

Example 1. Verification of Relationship Between MLPH Expression and Adipocyte Differentiation 1-1. Preparation of T3-L1 Cell Line 3T3-L1 is a mouse embryonic fibroblast cell line, and is mainly used as a model of metabolic disease and obesity studies. 3T3-L1 cell line purchased from ATCC was cultured in Dulbecco's modified Eagle's medium (DMEM) which includes bovine calf serum (BCS).

1-2. Induction of Differentiation into Adipocytes

To induce adipogenic differentiation, 2 more days after the 3T3-L1 cells reached confluency, an adipogenic differentiation inducer 0.5 mM 3-isobutyl-1-methyl-xanthine (IBMX, Sigma-Aldrich), and 1 μM dexamethasone (Dex, Sigma-Aldrich) and 10 μg/mL insulin (Sigma-Aldrich) were added to DMEM containing 10% FBS and were seeded in the cells. 2 days thereafter, the 3T3-L1 cells were further cultured in another 10% FBS-containing DMEM to induce differentiation into adipocytes (FIG. 1).

1-3. Measurement of MLPH Expression

Through RT-PCR (reverse transcriptase-polymerase chain reaction) using a Maxime PCR PreMix kit (Intron Biotechnology), real-time RT-PCR using KAPA SYBR FAST Universal qPCR kit (Kapa Biosystems), and CFX96 real-time RT-PCR detection system (BioRad), an RNA expression level of MLPH and PPARγ, FABP4, and adiponectin (regulatory factors of adipogenic differentiation) was measured. The primers used for the RT-PCR and the real-time RT-PCR are as shown in Tables 1 and 2, respectively.

TABLE 1

| Origin | Gene | Sequence forward | SEQ ID NO | Sequence reverse | SEQ ID NO |
|---|---|---|---|---|---|
| Mouse | MLPH | GCAGCCATGTAGCCCTTTAC | 1 | GGTGTCTACATCAGCCAGGT | 2 |
| | PPAR-γ | CCCTGGCAAAGCATTTGTAT | 3 | GAAACTGGCACCCTTGAAAA | 4 |
| | FABP4 | AAACACCGAGATTTCCTTCAAA | 5 | CACGCCTTTCATAACACATTC | 6 |
| | Adiponectin | GAGAAGGGAGAGAAAGGAGATG | 7 | TGAGCGATACACATAAGCGG | 8 |
| | RPL13A | CCTGCTGCTCTCAAGGTTGTT | 9 | CGATACTGCATCTTGGCCTTT | 10 |
| Human | MLPH | GGAGTGGTACTATGAGCATGTG | 11 | CTTCAAGATATCAGTTCAGGCCC | 12 |
| | PPAR-γ | GTCGGTTTCAGAAATGCCTTG | 13 | GCTGGTCGATATCACTGGAG | 14 |
| | FABP4 | CATGTGCAGAAATGGGATGG | 15 | AACTTCAGTCCAGGTCAACG | 16 |
| | ACC | GAGGGCTAGGTCTTTCTGGAG | 17 | CCACAGTGAAATCTCGTTGAGA | 18 |
| | β-actin | GCACCACACCTTCTACAATGA | 19 | TAGCACAGCCTGGATAGCAC | 20 |

TABLE 2

| Origin | Gene | Sequence forward | SEQ ID NO | Sequence reverse | SEQ ID NO |
|---|---|---|---|---|---|
| Mouse | MLPH | GAAGAAAGACTCCAGGGGCT | 21 | ACCACTCCAGAGAACCGATC | 22 |
| | PPAR-γ | CCCTGGCAAAGCATTTGTAT | 23 | GAAACTGGCACCCTTGAAAA | 24 |
| | FABP4 | AAACACCGAGATTTCCTTCAAA | 25 | CACGCCTTTCATAACACATTC | 26 |
| | Adiponectin | GAGAAGGGAGAGAAAGGAGATG | 27 | TGAGCGATACACATAAGCGG | 28 |
| | RPL13A | CCTGCTGCTCTCAAGGTTGTT | 29 | CGATAGTGCATCTTGGCCTTT | 30 |
| Human | MLPH | GCCCATCAAACCAACAGACA | 31 | TCCTCTGGTCTCTTGCCAAG | 32 |
| | PPAR-γ | TCATGGCAATTGAATGTCGT | 33 | CCAACAGCTTCTCCTTCTCG | 34 |
| | FABP4 | CATGGCCAAACCTAACATGA | 35 | AGTGACGCCTTTCATGACG | 36 |
| | β-actin | GGACTTCGAGCAAGAGATGG | 37 | AGCACTGTGTTGGCGTACAG | 38 |

Additionally, the expression level of MLPH protein was measured using Western blot which uses MLPH antibodies (Santa Cruz).

1-4. Increased MLPH Expression During Adipogenesis

As mentioned above, the differentiation into adipocytes was induced using the 3T3-L1 cell line, and during the differentiation into adipocytes, the expression of the MLPH gene of the present invention was confirmed to increase.

As a result of measuring the MLPH expression using RT-PCR (FIG. 2A), Western blot (FIG. 2C), and real-time quantitative RT-PCR (FIG. 2B) during the differentiation of the 3T3-L1 cells into adipocytes, a significant increase was shown on day 4 of differentiation.

Additionally, there was also an increase in the expression of PPARγ and FABP4, positive markers of differentiation into adipocytes, as the MLP (FIG. 2B).

Based on the experimental result above, the MLPH was confirmed to be involved in the differentiation into adipocytes. Whether the inhibition of MLPH would result in inhibition of adipogenesis was further to be confirmed.

Example 2. Verification of Relationship Between MLPH Inhibition and Fat Accumulation 2-1. Preparation of siRNA To confirm the effect of MLPH inhibition, siRNA was prepared. For the siRNA of MLPH, siRNA having SEQ ID NOS: 39 and 40 was used, and for the control, siRNA (si-Con) was purchased (Mbiotech).

TABLE 3

| siMLPH#1 | CAGAUCUUGGAGUUGAACAAGCGAA | SEQ ID NO: 39 |
|---|---|---|
| siMLPH#2 | CACAAUAACCACUAUCCACAA | SEQ ID NO: 40 |
| si-Con | CCUCGUGCCGUUCCAUCAGGUAGUU | SEQ ID NO: 43 |

2-2. Inhibition of MLPH Expression Using siRNA and Oil Red O Staining 100 nM siRNA was transfected into the same 3T3-L1 cell described above, and the cells were then induced to be differentiated into adipocytes. On day 8 of the differentiation, the fat was stained with Oil Red O dye (Sigma-Aldrich).

2-3. Inhibition of Differentiation into Adipocytes and Reduction of Fat Accumulation by Inhibiting MLPH Expression When the MLPH expression was inhibited using siRNA, its effects on fat accumulation were measured.

When the MLPH expression was inhibited using siRNA during the differentiation of 3T3-L1 into adipocytes, the level of fat was reduced. As a result of observation with the naked eye (FIG. 3A), quantification of the degree of fat staining (FIG. 3B), and observation with a microscope (FIG. 3C), fat accumulation (lipid droplet) was reduced.

2-4. Reduction of Expression of Regulatory Factor for Adipogenic Differentiation by Inhibiting MLPH Expression After the treatment with siRNA for the inhibition of the MLPH expression, the expression level of RNA of each gene was measured using RT-PCR (A) and real-time RT-PCR (B), and the protein expression level was measured using Western blot (C).

As a result, gene and protein expressions of PPARγ, FABP4, and adiponectin, which are known as important regulatory factors of differentiation during adipogenic differentiation, were reduced (FIG. 4).

2-5. Experiment on MLPH-siRNA Cytotoxicity

An experiment was performed as below to verify whether the inhibition of adipocyte differentiation was due to the cytotoxicity of MLPH-siRNA.

$1 \times 10^4$ of the 3T3-L1 cells were inoculated in a 12-well plate, and MLPH gene expression was inhibited using Lipofectamine RNAi MAX reagent (Invitrogen) on the next day.

The plate was fixed using 3.7% formalin (JUNSEI) 24 hours and 120 hours later, and then stained using 0.01% crystal violet.

As a result, there was no difference in cell proliferation between siRNA-treated cells and cells not treated with siRNA, thereby confirming that the siRNA treatment would have no effect on cell proliferation. In other words, the inhibition of the adipocyte differentiation is not due to the cytotoxicity of siRNA (FIG. 5).

Example 3. Increase in MLPH Expression by Free Fatty Acid Treatment

To determine whether MLPH is involved in fatty acid accumulation, oleic acid was treated in HepG2 and SNU475 liver cancer cell lines, and the MLPH expression was measured.

Oleic acid powder (Sigma-Aldrich), a type of free fatty acid, was dissolved at a concentration of 500 mM using DMSO. The 500 mM oleic acid was dissolved in 10% BSA and added to the medium. When the cells reached about 70% confluency, the oleic acid was treated to have a concentration of 500 mM.

The Oil Red O staining was increased due to the treatment of oleic acid, suggesting that fat had efficiently accumulated. The expression of MLPH was increased, as well as that of PPARγ, ACC1, and FAS, markers of fatty acid accumulation (FIG. 6).

Additionally, when a condition of hepatic steatosis, which appears as obesity advances, was set in an in vitro model, the MLPH expression was confirmed to increase, which indicates that MLPH is involved in not only fat accumulation but also hepatic steatosis by adipogenic differentiation.

Example 4. Increase in MLPH Expression During Fat Accumulation of Human Cells and Differentiation Thereof into Adipocytes To determine relevance of human cells' fat accumulation and differentiation into adipocytes with MLPH, an MLPH expression level was measured during the differentiation of human mesenchymal stem cells.

Specifically, the human mesenchymal stem cells were cultured in a culture medium for adipocyte differentiation to induce differentiation into adipocytes, and accumulated fat was stained with Oil Red O dye. The mRNA expression level of MLPH and PPARγ (i.e., a known regulatory factor of adipogenic differentiation) was then measured using a real-time RT-PCR method.

Based on the result of the Oil Red staining of the human mesenchymal stem cells, it was confirmed that differentiation into adipocytes had been induced (A of FIG. 7).

Further, 24 hours after the differentiation had been induced, the MLPH expression was greatly increased, as well as the PPARγ expression, wherein the PPARγ is a known regulatory factor of adipogenetic differentiation, thereby confirming that the adipogenic differentiation had been induced (B and C of FIG. 7).

In light of the above, MLPH was confirmed to be involved in the differentiation into adipocytes and also fat accumulation in human cells.

Example 5. Role of MLPH in Differentiation of Human Cells into Adipocytes

To specifically determine a role of MLPH involved in the differentiation into adipocytes and fat accumulation of human cells, the degrees of fat accumulation and differentiation into adipocytes were measured.

MLPH siRNA (#1 siRNA, 5'-GAG CAU GUG AAA GCC CGC UUC AAG A-3', SEQ ID NO: 41: #2 siRNA, 5'-CCC UAU CUU CUG AGA AGA AAG UUC A-3', SEQ ID NO: 42) and the control siRNA (SEQ ID NO: 43) were treated in the cells, and the expression level of mRNA of each gene was measured using real-time RT-PCR (A to C of FIG. 8), and the fat was stained using Oil Red O dye 5 days after differentiation had initiated (D of FIG. 8).

As a result, when MLPH deficiency was induced, the expression of PPARγ (an adipocyte differentiation marker) was greatly reduced, and at the same time, the degree of the Oil Red O staining was significantly reduced.

Based on the result, it was confirmed that the fat accumulation of human cells and differentiation thereof into adipocytes are inhibited under the MPLH-deficient condition.

Accordingly, MLPH was confirmed to be a key factor in the fat accumulation and differentiation into adipocytes.

It was confirmed from the Examples above that by inhibiting the MLPH gene expression, obesity can be prevented or treated, or by measuring the expression level thereof, a therapeutic agent for obesity can be screened.

Those of ordinary skill in the art will recognize that the present invention may be embodied in other specific forms without departing from its spirit or essential characteristics. The described embodiments are to be considered in all respects only as illustrative and not restrictive. The scope of the present invention is therefore indicated by the appended claims rather than by the foregoing description. All changes which come within the meaning and range of equivalency of the claims are to be embraced within the scope of the present invention.

What is claimed is:

1. A method for screening for a therapeutic agent for preventing or treating obesity, comprising:
   (a) providing or having provided a cell capable of differentiating into an adipocyte in which a melanophilin (MLPH) gene is expressed,
   wherein the cell capable of differentiating into an adipocyte is an embryonic fibroblast cell or a human mesenchymal stem cell;
   (b) contacting a candidate therapeutic agent for obesity with the cell,
   wherein the therapeutic agent is selected from the group consisting of microRNA, siRNA, shRNA, an antibody, and an aptamer;
   (c) measuring an expression level or activity of a MLPH protein or a gene encoding the MLPH protein in the cell contacted with the candidate therapeutic agent for obesity in (a); and
   (d) determining that the candidate therapeutic agent for obesity is a therapeutic agent for obesity when the expression level or activity of the MLPH protein or gene measured in (b) decreases compared to that of a control cell not contacted with the candidate therapeutic agent, wherein the control cell is the same type of cell as provided in (a) and the control cell is grown or cultured under substantially the same conditions as the cell contacted with the candidate therapeutic agent for obesity.

2. The method of claim 1, wherein measuring the expression level or activity of the MLPH protein or gene is to measure the expression level of the MLPH protein.

3. The method of claim 2, wherein the expression level of the MLPH protein is measured by using an antibody, an aptamer, an antagonist, or a combination thereof.

4. The method of claim 1, wherein the therapeutic agent for obesity inhibits adipocyte differentiation.

5. The method of claim 1, wherein measuring the expression level or activity of the MLPH protein or gene is to measure the expression level of an mRNA of the MLPH gene.

6. The method of claim 3, wherein the expression level of the MLPH protein is measured by using an antibody.

7. The method of claim 3, wherein the expression level of the MLPH protein is measured by using an aptamer.

8. The method of claim 3, wherein the expression level of the MLPH protein is measured by using an antagonist.

9. The method of claim 1, wherein the therapeutic agent for obesity inhibits fat accumulation.

10. The method of claim 5, wherein the expression level of the mRNA of the MLPH gene is measured by using an anti-sense oligonucleotide, a pair of primers, a probe, or a combination thereof.

11. The method of claim 1, wherein the cell capable of differentiating into an adipocyte is an embryonic fibroblast cell.

12. The method of claim 11, wherein the cell capable of differentiating into an adipocyte is a human mesenchymal stem cell.

* * * * *

SEQUENCE LISTING

<160> NUMBER OF SEQ ID NOS: 43

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonucleotide: MLPH forward primer

<400> SEQUENCE: 1
gcagccatgt agccctttac                                                 20

<210> SEQ ID NO 2
<211> LENGTH: 20
<212> TYPE: DNA
<213> ORGANISM: Artificial Sequence
<220> FEATURE:
<223> OTHER INFORMATION: Synthetic oligonucleotide: MLPH reverse primer

<400> SEQUENCE: 2
ggtgtctaca tcagccaggt                                                 20

<210> SEQ ID NO 3
<211> LENGTH: 20
<212> TYPE: DNA
<213> ORGANISM: Artificial Sequence
<220> FEATURE:
<223> OTHER INFORMATION: Synthetic oligonucleotide: PPAR-gamma forward
    primer

<400> SEQUENCE: 3
ccctggcaaa gcatttgtat                                                 20

<210> SEQ ID NO 4
<211> LENGTH: 20
<212> TYPE: DNA
<213> ORGANISM: Artificial Sequence
<220> FEATURE:
<223> OTHER INFORMATION: Synthetic oligonucleotide: PPAR-gamma reverse
    primer

<400> SEQUENCE: 4
gaaactggca cccttgaaaa                                                 20

<210> SEQ ID NO 5
<211> LENGTH: 22
<212> TYPE: DNA
<213> ORGANISM: Artificial Sequence
<220> FEATURE:
<223> OTHER INFORMATION: Synthetic oligonucleotide: FABP4 forward primer

<400> SEQUENCE: 5
aaacaccgag atttccttca aa    22

<210> SEQ ID NO 6
<211> LENGTH: 21
<212> TYPE: DNA
<213> ORGANISM: Artificial Sequence
<220> FEATURE:
<223> OTHER INFORMATION: Synthetic oligonucleotide: FABP4 reverse primer

<400> SEQUENCE: 6
cacgcctttc ataacacatt c    21

<210> SEQ ID NO 7
<211> LENGTH: 22
<212> TYPE: DNA
<213> ORGANISM: Artificial Sequence
<220> FEATURE:
<223> OTHER INFORMATION: Synthetic oligonucleotide: Adiponectin forward primer

<400> SEQUENCE: 7
gagaagggag agaaaggaga tg    22

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide: Adiponectin reverse primer

<400> SEQUENCE: 8
tgagcgatac acataagcgg    20

<210> SEQ ID NO 9
<211> LENGTH: 21
<212> TYPE: DNA
<213> ORGANISM: Artificial Sequence
<220> FEATURE:
<223> OTHER INFORMATION: Synthetic oligonucleotide: RPL13A forward primer

<400> SEQUENCE: 9
cctgctgctc tcaaggttgt t    21

<210> SEQ ID NO 10
<211> LENGTH: 21
<212> TYPE: DNA
<213> ORGANISM: Artificial Sequence
<220> FEATURE:
<223> OTHER INFORMATION: Synthetic oligonucleotide: RPL13A reverse primer

<400> SEQUENCE: 10
cgatactgca tcttggcctt t    21

-continued

```
<210> SEQ ID NO 11
<211> LENGTH: 22
<212> TYPE: DNA
<213> ORGANISM: Artificial Sequence
<220> FEATURE:
<223> OTHER INFORMATION: Synthetic oligonucleotide: MLPH forward primer

<400> SEQUENCE: 11
ggagtggtac tatgagcatg tg                                              22

<210> SEQ ID NO 12
<211> LENGTH: 23
<212> TYPE: DNA
<213> ORGANISM: Artificial Sequence
<220> FEATURE:
<223> OTHER INFORMATION: Synthetic oligonucleotide: MLPH reverse primer

<400> SEQUENCE: 12
cttcaagata tcagttcagg ccc                                             23

<210> SEQ ID NO 13
<211> LENGTH: 21
<212> TYPE: DNA
<213> ORGANISM: Artificial Sequence
<220> FEATURE:
<223> OTHER INFORMATION: Synthetic oligonucleotide: PPAR-gamma forward
      primer

<400> SEQUENCE: 13
gtcggtttca gaaatgcctt g                                               21

<210> SEQ ID NO 14
<211> LENGTH: 20
<212> TYPE: DNA
<213> ORGANISM: Artificial Sequence
<220> FEATURE:
<223> OTHER INFORMATION: Synthetic oligonucleotide: PPAR-gamma reverse
      primer

<400> SEQUENCE: 14
gctggtcgat atcactggag                                                 20

<210> SEQ ID NO 15
<211> LENGTH: 20
<212> TYPE: DNA
<213> ORGANISM: Artificial Sequence
<220> FEATURE:
<223> OTHER INFORMATION: Synthetic oligonucleotide: FABP4 forward
      primer

<400> SEQUENCE: 15
catgtgcaga aatgggatgg                                                 20

<210> SEQ ID NO 16
<211> LENGTH: 20
<212> TYPE: DNA
<213> ORGANISM: Artificial Sequence
<220> FEATURE:
<223> OTHER INFORMATION: Synthetic oligonucleotide: FABP4 reverse
      primer

<400> SEQUENCE: 16
aacttcagtc caggtcaacg                                                 20

<210> SEQ ID NO 17
<211> LENGTH: 21
```

```
<212> TYPE: DNA
<213> ORGANISM: Artificial Sequence
<220> FEATURE:
<223> OTHER INFORMATION: Synthetic oligonucleotide: ACC forward primer

<400> SEQUENCE: 17
gagggctagg tctttctgga g                                        21

<210> SEQ ID NO 18
<211> LENGTH: 22
<212> TYPE: DNA
<213> ORGANISM: Artificial Sequence
<220> FEATURE:
<223> OTHER INFORMATION: Synthetic oligonucleotide: ACC reverse primer

<400> SEQUENCE: 18
ccacagtgaa atctcgttga ga                                       22

<210> SEQ ID NO 19
<211> LENGTH: 21
<212> TYPE: DNA
<213> ORGANISM: Artificial Sequence
<220> FEATURE:
<223> OTHER INFORMATION: Synthetic oligonucleotide: beta-actin forward
      primer

<400> SEQUENCE: 19
gcaccacacc ttctacaatg a                                        21

<210> SEQ ID NO 20
<211> LENGTH: 21
<212> TYPE: DNA
<213> ORGANISM: Artificial Sequence
<220> FEATURE:
<223> OTHER INFORMATION: Synthetic oligonucleotide: beta-actin reverse
      primer

<400> SEQUENCE: 20
tagcacagcc tggatagcaa c                                        21

<210> SEQ ID NO 21
<211> LENGTH: 20
<212> TYPE: DNA
<213> ORGANISM: Artificial Sequence
<220> FEATURE:
<223> OTHER INFORMATION: Synthetic oligonucleotide: MLPH forward primer

<400> SEQUENCE: 21
gaagaaagac tccaggggct                                          20

<210> SEQ ID NO 22
<211> LENGTH: 20
<212> TYPE: DNA
<213> ORGANISM: Artificial Sequence
<220> FEATURE:
<223> OTHER INFORMATION: Synthetic oligonucleotide: MLPH reverse primer

<400> SEQUENCE: 22
accactccag agaaccgatc                                          20

<210> SEQ ID NO 23
<211> LENGTH: 20
<212> TYPE: DNA
<213> ORGANISM: Artificial Sequence
<220> FEATURE:
<223> OTHER INFORMATION: Synthetic oligonucleotide: PPAR-gamma forward
      primer
```

<400> SEQUENCE: 23
ccctggcaaa gcatttgtat                                               20

<210> SEQ ID NO 24
<211> LENGTH: 20
<212> TYPE: DNA
<213> ORGANISM: Artificial Sequence
<220> FEATURE:
<223> OTHER INFORMATION: Synthetic oligonucleotide: PPAR-gamma reverse
      primer

<400> SEQUENCE: 24
gaaactggca cccttgaaaa                                               20

<210> SEQ ID NO 25
<211> LENGTH: 22
<212> TYPE: DNA
<213> ORGANISM: Artificial Sequence
<220> FEATURE:
<223> OTHER INFORMATION: Synthetic oligonucleotide: FABP4 forward
      primer

<400> SEQUENCE: 25
aaacaccgag atttccttca aa                                            22

<210> SEQ ID NO 26
<211> LENGTH: 21
<212> TYPE: DNA
<213> ORGANISM: Artificial Sequence
<220> FEATURE:
<223> OTHER INFORMATION: Synthetic oligonucleotide: FABP4 reverse
      primer

<400> SEQUENCE: 26
cacgcctttc ataacacatt c                                             21

<210> SEQ ID NO 27
<211> LENGTH: 22
<212> TYPE: DNA
<213> ORGANISM: Artificial Sequence
<220> FEATURE:
<223> OTHER INFORMATION: Synthetic oligonucleotide: Adiponectin forward
      primer

<400> SEQUENCE: 27
gagaagggag agaaaggaga tg                                            22

<210> SEQ ID NO 28
<211> LENGTH: 20
<212> TYPE: DNA
<213> ORGANISM: Artificial Sequence
<220> FEATURE:
<223> OTHER INFORMATION: Synthetic oligonucleotide: Adiponectin reverse
      primer

<400> SEQUENCE: 28
tgagcgatac acataagcgg                                               20

<210> SEQ ID NO 29
<211> LENGTH: 21
<212> TYPE: DNA
<213> ORGANISM: Artificial Sequence
<220> FEATURE:
<223> OTHER INFORMATION: Synthetic oligonucleotide: RPL13A forward
      primer

<400> SEQUENCE: 29
cctgctgctc tcaaggttgt t                                              21

<210> SEQ ID NO 30
<211> LENGTH: 21
<212> TYPE: DNA
<213> ORGANISM: Artificial Sequence
<220> FEATURE:
<223> OTHER INFORMATION: Synthetic oligonucleotide: RPL13A reverse
      primer

<400> SEQUENCE: 30
cgatagtgca tcttggcctt t                                              21

<210> SEQ ID NO 31
<211> LENGTH: 20
<212> TYPE: DNA
<213> ORGANISM: Artificial Sequence
<220> FEATURE:
<223> OTHER INFORMATION: Synthetic oligonucleotide: MLPH forward primer

<400> SEQUENCE: 31
gcccatcaaa ccaacagaca                                                20

<210> SEQ ID NO 32
<211> LENGTH: 20
<212> TYPE: DNA
<213> ORGANISM: Artificial Sequence
<220> FEATURE:
<223> OTHER INFORMATION: Synthetic oligonucleotide: MLPH reverse primer

<400> SEQUENCE: 32
tcctctggtc tcttgccaag                                                20

<210> SEQ ID NO 33
<211> LENGTH: 20
<212> TYPE: DNA
<213> ORGANISM: Artificial Sequence
<220> FEATURE:
<223> OTHER INFORMATION: Synthetic oligonucleotide: PPAR-gamma forward
      primer

<400> SEQUENCE: 33
tcatggcaat tgaatgtcgt                                                20

<210> SEQ ID NO 34
<211> LENGTH: 20
<212> TYPE: DNA
<213> ORGANISM: Artificial Sequence
<220> FEATURE:
<223> OTHER INFORMATION: Synthetic oligonucleotide: PPAR-gamma reverse
      primer

<400> SEQUENCE: 34
ccaacagctt ctccttctcg                                                20

<210> SEQ ID NO 35
<211> LENGTH: 20
<212> TYPE: DNA
<213> ORGANISM: Artificial Sequence
<220> FEATURE:
<223> OTHER INFORMATION: Synthetic oligonucleotide: FABP4 forward
      primer

<400> SEQUENCE: 35
catggccaaa cctaacatga                                                20

<210> SEQ ID NO 36
<211> LENGTH: 19
<212> TYPE: DNA
<213> ORGANISM: Artificial Sequence
<220> FEATURE:
<223> OTHER INFORMATION: Synthetic oligonucleotide: FABP4 reverse primer

<400> SEQUENCE: 36
agtgacgcct ttcatgacg                                           19

<210> SEQ ID NO 37
<211> LENGTH: 20
<212> TYPE: DNA
<213> ORGANISM: Artificial Sequence
<220> FEATURE:
<223> OTHER INFORMATION: Synthetic oligonucleotide: beta-actin forward primer

<400> SEQUENCE: 37
ggacttcgag caagagatgg                                          20

<210> SEQ ID NO 38
<211> LENGTH: 20
<212> TYPE: DNA
<213> ORGANISM: Artificial Sequence
<220> FEATURE:
<223> OTHER INFORMATION: Synthetic oligonucleotide: beta-actin reverse primer

<400> SEQUENCE: 38
agcactgtgt tggcgtacag                                          20

<210> SEQ ID NO 39
<211> LENGTH: 25
<212> TYPE: RNA
<213> ORGANISM: Artificial Sequence
<220> FEATURE:
<223> OTHER INFORMATION: Synthetic oligonucleotide: siMLPH#1

<400> SEQUENCE: 39
cagaucuugg aguugaacaa gcgaa                                    25

<210> SEQ ID NO 40
<211> LENGTH: 21
<212> TYPE: RNA
<213> ORGANISM: Artificial Sequence
<220> FEATURE:
<223> OTHER INFORMATION: Synthetic oligonucleotide: siMLPH#2

<400> SEQUENCE: 40
cacaauaacc acuauccaca a                                        21

<210> SEQ ID NO 41
<211> LENGTH: 25
<212> TYPE: RNA
<213> ORGANISM: Artificial Sequence
<220> FEATURE:
<223> OTHER INFORMATION: Synthetic oligonucleotide: hsiMLPH#1

<400> SEQUENCE: 41
gagcauguga agcccgcuu caaga                                     25

<210> SEQ ID NO 42
<211> LENGTH: 25

```
<212> TYPE: RNA
<213> ORGANISM: Artificial Sequence
<220> FEATURE:
<223> OTHER INFORMATION: Synthetic oligonucleotide:  hsiMLPH#2

<400> SEQUENCE: 42
cccuaucuuc ugagaagaaa guuca                                              25

<210> SEQ ID NO 43
<211> LENGTH: 25
<212> TYPE: RNA
<213> ORGANISM: Artificial Sequence
<220> FEATURE:
<223> OTHER INFORMATION: Synthetic oligonucleotide:  si-Con

<400> SEQUENCE: 43
ccucgugccg uuccaucagg uaguu                                              25
```